United States Patent
Coupard et al.

(10) Patent No.: US 8,309,781 B2
(45) Date of Patent: Nov. 13, 2012

(54) PROCESS FOR THE PRODUCTION OF LIGHT OLEFINS FROM ETHANOL IN THE PRESENCE OF A MACROPOROUS CATALYST THAT COMES IN THE FORM OF BALLS

(75) Inventors: Vincent Coupard, Valencin (FR); Emmanuelle Guillon, Vernaison (FR); Sylvie Maury, Charly (FR); Nicolas Cadran, Oullins (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 94 days.

(21) Appl. No.: 12/851,861

(22) Filed: Aug. 6, 2010

(65) Prior Publication Data
US 2011/0034750 A1    Feb. 10, 2011

(30) Foreign Application Priority Data
Aug. 7, 2009  (FR) ..................... 09 03910

(51) Int. Cl.
*C07C 1/20*  (2006.01)
(52) U.S. Cl. ................. 585/638; 585/639; 585/640
(58) Field of Classification Search ............ 585/638, 585/639, 640, 648, 653; 502/64, 77
See application file for complete search history.

(56) References Cited

U.S. PATENT DOCUMENTS

| 4,621,164 A | 11/1986 | Chang et al. | |
|---|---|---|---|
| 7,880,048 B2 * | 2/2011 | Pigeat et al. | 585/648 |
| 2006/0235251 A1 * | 10/2006 | Dath et al. | 585/639 |
| 2007/0027351 A1 * | 2/2007 | Dath et al. | 585/639 |
| 2009/0088595 A1 | 4/2009 | Pigeat et al. | |

FOREIGN PATENT DOCUMENTS

| EP | 1 892 229 A1 | 2/2008 |
|---|---|---|
| FR | 2 905 122 A1 * | 2/2008 |
| JP | 2007-290991 A | 11/2007 |

OTHER PUBLICATIONS

Search Report of FR 0903910 (May 7, 2010).

* cited by examiner

*Primary Examiner* — Tam M Nguyen
(74) *Attorney, Agent, or Firm* — Millen, White, Zelano & Branigan, P.C.

(57) ABSTRACT

A process for the production of C3-C6 light olefins from ethanol is described, and said process comprises at least the passage of a feedstock that contains ethanol into at least one reaction unit that is provided with at least one catalyst that comes in the form of spherical balls with a diameter of between 1 and 3 mm, each of said spherical balls comprising at least one zeolite and at least one alumina-based substrate and having a pore distribution such that the macropore volume that is measured by mercury porosimetry is between 0.10 and 0.20 ml/g and the mesopore volume that is measured by mercury porosimetry is between 0.25 and 0.35 ml/g.

16 Claims, No Drawings

PROCESS FOR THE PRODUCTION OF LIGHT OLEFINS FROM ETHANOL IN THE PRESENCE OF A MACROPOROUS CATALYST THAT COMES IN THE FORM OF BALLS

FIELD OF THE INVENTION

This invention relates to the field of the production of C3-C6 light olefins from the conversion of ethanol. The process for the production of olefins according to the invention addresses various ethanol feedstocks, optionally produced by biological means. It uses at least one catalyst in the form of spherical balls that is prepared in the presence of a pore-forming agent so as to create macroporous fields within the pores of each of said balls. The light olefins that are obtained by the process of the invention can easily be upgraded as a base for fuel or for petrochemical applications.

PRIOR ART

The reaction on which the process for transforming ethanol into hydrocarbons is based is the dehydration-oligomerization in one stage of ethanol according to equation (1) below:

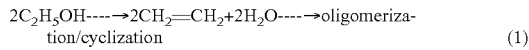

$$2C_2H_5OH \longrightarrow 2CH_2=CH_2+2H_2O \longrightarrow \text{oligomerization/cyclization} \qquad (1)$$

The oligomerization stage leads to the production of light olefins, the types sought for the purpose of subsequent applications, while the cyclization constitutes a non-selective reaction that leads to the undesirable production of aromatic, naphthenic and paraffinic compounds.

The reaction for transformation of ethanol for producing hydrocarbons has been studied on zeolitic catalysts, primarily on the ZSM-5 zeolite. It most often leads to the production of very strongly aromatic effluents.

In the 1980s, the process entitled BTG (Bioethanol-To-Gasoline) was announced for transforming ethanol originating from natural carbohydrates into gasoline (D. R. Whitcraft, X. E. Verykios, et al. (1983), "Recovery of Ethanol from Fermentation Broths by Catalytic Conversion to Gasoline," *Industrial & Engineering Chemistry Process Design and Development* 22(3): 452-457). Later, in the 1990s, it was shown that it was possible to use ethanol to transform it by heterogeneous catalysis into compounds having long carbon chains (S. Saha and S. Sivasanka (1992), *Indian Journal of Technology* 30: 71).

The transformation of alcohols into hydrocarbons is a field that has already been the subject of patents. For example, the U.S. Pat. No. 3,899,544 describes a process for the transformation of alcohols and/or ethers on zeolitic catalysts, in particular ZSM-5. The U.S. Pat. No. 4,621,164 describes a process for conversion of ethanol for the production of gasoline bases. The patent application U.S. 2006/0235251 describes a process that uses an MFI catalyst that is shaped in a silica-based matrix or AlPO$_4$. However, these catalysts are not satisfactory in terms of selectivity: either they promote the predominant production of undesirable compounds, in particular aromatic compounds, at the expense of the production of light olefins, or they have a very high selectivity in terms of ethylene production, at the expense of oligomers, in particular C3-C6 olefins. Ethylene is expensive, in terms of installation and energy, in isolating and separating said oligomers. The selective transformation of ethanol in terms of said oligomers would make it possible to envisage less energy-hungry means of transformation.

Also, this invention proposes to provide a process for production of light olefins from the transformation of ethanol that leads to an improved production of olefins having 3 to 6 carbon atoms per molecule relative to the known processes of the prior art.

OBJECT AND ADVANTAGE OF THE INVENTION

This invention has as its object a process for the production of C3-C6 light olefins from ethanol comprising at least:

1) The passage of a feedstock that contains ethanol into at least one reaction unit that is provided with at least one catalyst that comes in the form of spherical balls with a diameter of between 1 and 3 mm, whereby each of said spherical balls comprises at least one zeolite and at least one alumina-based substrate and has a pore distribution such that the macropore volume that is measured by mercury porosimetry is between 0.10 and 0.20 ml/g, and the mesopore volume that is measured by mercury porosimetry is between 0.25 and 0.35 ml/g, so as to produce at least one gas effluent that comprises at least said C3-C6 light olefins, and 2) The separation of the gas effluent that is obtained in stage 1) so as to collect at least one gaseous fraction that comprises said light olefins, whereby at least one organic liquid fraction comprises compounds that have a boiling point that is less than 150° C. and at least one aqueous liquid effluent.

The process according to the invention, implemented in the presence of a macroporous catalyst that comes in the form of spherical balls, offers the advantage of limiting the production of undesirable by-products, in particular aromatic compounds, by promoting the selectivity in terms of the C3-C6 light olefins. The effect is an improvement of the yield of the process according to the invention in terms of said olefins. Furthermore, it was discovered, surprisingly enough, that said macroporous catalyst leads to improved performances in terms of activity for the conversion of ethylene, produced by dehydration of ethanol (according to equation (1) described above), into desired C3-C6 light olefins. This thus gives rise to the production of an effluent that is composed for the most part of said olefins, in which the presence of ethylene is reduced, and consequently the possibility of directly upgrading said effluent without the necessity of implementing a separation stage of the ethylene, which is difficult to implement.

DETAILED DESCRIPTION OF THE INVENTION

This invention has as its object a process for the production of C3-C6 light olefins from ethanol comprising at least:

1) The passage of a feedstock that contains ethanol into at least one reaction unit that is provided with at least one catalyst that comes in the form of spherical balls with a diameter of between 1 and 3 mm, each of said spherical balls comprising at least one zeolite and at least one alumina-based substrate and having a pore distribution such that the macropore volume that is measured by mercury porosimetry is between 0.10 and 0.20 ml/g and the mesopore volume that is measured by mercury porosimetry is between 0.25 and 0.35 ml/g, so as to produce at least one gas effluent that comprises at least said C3-C6 light olefins, and 2) The separation of the gas effluent that is obtained in stage 1) so as to collect at least one gaseous fraction that comprises said light olefins, at least one organic liquid fraction that comprises compounds that have a boiling point that is less than 150° C. and at least one aqueous liquid effluent.

The object of the process according to the invention is the production of light olefins that have a chain length of between 3 and 6 carbon atoms (C3-C6 olefins) from the selective conversion of a feedstock that contains ethanol. Said light olefins are generated in situ following a succession of transformations implemented in a single stage within at least one reaction unit that can contain several reactors so as to keep the reaction temperature constant. More specifically, in a first step, ethanol is dehydrated into ethylene, which is transformed, under the same operating conditions as those of the dehydration and on the same catalyst, in the presence of water that is released by the dehydration reaction, into oligomers, i.e., into C3-C6 light olefins. The degradation of said light olefins into paraffins, naphthenes and aromatic compounds constitutes a parasitic consecutive reaction, which is consequently undesirable.

According to the invention, said feedstock that is treated in the reaction unit that is used for the implementation of stage 1) of the process for production of light olefins according to the invention contains ethanol, whose proportion in said feedstock can be variable. The reaction unit can be supplied by a feedstock that consists entirely of ethanol. Preferably, said feedstock comprises ethanol and water, with ethanol representing at least 10% by mass, preferably at least 40% by mass of said dilute feedstock. The process of the invention applies to various ethanol feedstocks that can contain variable amounts of water. In particular, according to a particular embodiment of the process of the invention, the feedstock that supplies said reaction unit comprises at least 50% by weight of water and preferably at least 60% by weight of water. The ethanol that is present in said feedstock can have various sources; in particular, it may have been produced by biological means, for example by fermentation of sugar, or it may have been obtained from a process for transformation by chemical means. Said feedstock that supplies the process of the invention can also advantageously be obtained from biomass.

In the cases where the ethanol is obtained from a source in which it is found in the presence of impurities, in particular organic impurities such as acids, heavy alcohols and aldehydes, or inorganic impurities such as nitrogen, sodium, or phosphorus, or metal impurities such as manganese, iron, copper or zinc, it is advisable to initiate a purification of ethanol so as to use a feedstock that is substantially free of said impurities. Ethanol purification methods are described in the Ullman Encyclopedia (©2007 Wiley-VCH Verlag GmbH & Co. KGaA, Weinheim, Chapter 6) and can be applied within the scope of this invention.

According to the invention, the feedstock that contains ethanol, supplying the reaction unit that is employed for the implementation of said stage 1) of the process for production of light olefins according to the invention, is free of olefins.

The reaction unit that is employed for the implementation of said stage 1) of the process for production of light olefins according to the invention advantageously performs at a temperature of between 300 and 600° C., preferably between 450 and 575° C., under a pressure of between 0.1 and 1.5 MPa, preferably between 0.1 and 0.5 MPa, with an hourly speed by weight (weight of feedstock per weight of catalyst and per hour) of between 0.1 and 10 $h^{-1}$, preferably between 1 and 4 $h^{-1}$.

The catalyst, used in each of the reactors of the reaction unit of the process of the invention, comes in the form of spherical balls having a double porosity measured by mercury porosimetry: a macroporosity that is characterized by a macroporous mercury volume in a range that varies from 0.10 to 0.20 ml/g, preferably in a range that varies from 0.12 to 0.18 ml/g, and a mesoporosity that is characterized by a mesoporous mercury volume in a range that varies from 0.25 to 0.35 ml/g, preferably in a range that varies from 0.28 to 0.35 ml/g. The macroporosity is also characterized by the presence of macroporous fields beyond 50 nm, preferably beyond 100 nm, and/or results from an intraparticulate textural macroporosity; the mesoporosity is also characterized by the presence of mesoporous fields in a range that varies from 7 to 50 nm and preferably in a range that varies from 8 to 10 nm. The proportion of the pore volume of said balls having a pore size that is less than 20 nm is between 60 and 70%.

The mercury porosimetry analysis corresponds to the intrusion of a mercury volume that is characteristic of the existence of mesopores and macropores in said catalyst according to the standard ASTM D4284-83 at a maximum pressure of 4,000 bar, using a surface tension of 484 dynes/cm and a contact angle of 140° (a value that is selected according to the recommendation of the work "Technique de l'ingénieur, traité analyse et caractérisation [Engineering Techniques, Analytical Treatise and Characterization]," page 1050, written by J. Charpin and B. Rasneur), and the pores being assumed to be cylindrical in shape. This technique makes it possible to access the value of the mesoporous mercury volume that is defined as being the mercury volume that is adsorbed by all of the pores having a diameter in the range of mesopores, namely between 3.6 and 50 nm. Likewise, the macroporous mercury volume is defined as being the mercury volume that is adsorbed by all of the pores having a diameter of greater than 50 nm.

According to the invention, the zeolite that is present in each of said spherical balls forming the catalyst is preferably selected from among the zeolites of the structural type MEL, MFI, NES, EUO, FER, CHA, MFS, MWW and NES, and very preferably, it involves an WI-structural-type zeolite, in particular the ZSM-5 zeolite. Said zeolite can also advantageously be selected from among the NU-85, NU-86 and IM-5 zeolites. Advantageously, said zeolite that is present in each of said spherical balls forming the catalyst has an Si/Al ratio of between 50 and 500 and very advantageously between 70 and 140. Said zeolite is dispersed in an alumina-based substrate within each of said spherical balls forming the catalyst. The proportion of zeolite in each of said balls forming the catalyst is between 15 and 90% by weight, preferably between 30 and 80% by weight, and very preferably between 35 and 50% by weight, whereby the remainder consists of the alumina-based substrate.

According to the invention, said spherical balls that constitute said catalyst that is used in the process of the invention have a diameter of between 1 and 3 mm, preferably between 1.8 and 2.2 mm. The morphology and the size distribution of the balls are established by analysis of photos obtained by Scanning Electroscopic Microscopy (SEM). The catalyst has a specific surface area $S_{BET}$ of between 290 and 350 $m^2/g$. It has a mechanical resistance that is measured by grain-to-grain crushing, according to the ASTM D4179-88a method, such that EGG is at least equal to 10 N and preferably at least equal to 20 N.

The catalyst is prepared according to a process that comprises a) the preparation of at least one emulsion that is formed by at least one pore-forming agent, water and a surfactant, b) the preparation of a suspension that is formed by water, acid, an alumina source, at least one zeolite, and said emulsion that is prepared during stage a), c) the shaping by drop coagulation consisting in i) passing said suspension that is formed in b) into a draining pot that consists of nozzles that each have an orifice of calibrated size so as to form droplets, ii) passing, in a downward motion, said droplets into a column that contains an upper phase that consists of an organic phase and a lower phase that consists of a basic aqueous phase, whereby the organic phase-aqueous phase interface consists of a surfactant, so as to collect spherical balls, d) the drying of said balls, and e) the calcination of said balls.

For the preparation of the emulsion according to stage a), the pore-forming agent, used to form pores in the balls of the final catalyst, is a petroleum fraction, preferably a paraffinic kerosene fraction that has 10 to 14 carbon atoms, formed by normal paraffin and iso-paraffins, and having a boiling point of between 220 and 350° C. A commercial compound, Isane®, marketed by the Total Company, whose composition does not comprise more than 5 ppm by mass of aromatic compounds, is advantageously used as a pore-forming agent. The surfactant, used for the preparation of the emulsion, is a non-ionic emulsifying agent. It is selected so as to ensure the stability of the emulsion. It is also selected so as to be eliminated by combustion and to be found in liquid form at ambient temperature. A commercialized compound, Galoryl®, sold by the Comptoir Français des Produits Industriels, is generally selected as surfactant. The mixing of water, a pore-forming agent, and surfactant is done at ambient temperature for a period of preferably between 10 and 15 minutes.

In a first step, the preparation of the suspension according to stage b) consists in mixing water, acid, and the alumina source and then in introducing into the thus formed mixture at least one zeolite and finally introducing therein the emulsion that is formed during stage a). The mixing of water, acid and the alumina source is done at ambient temperature. The water and the acid are mixed simultaneously, and then the alumina source is introduced. The acid that is used for the preparation of the suspension is advantageously selected from among strong acids, preferably nitric acid and sulfuric acid. Very advantageously, nitric acid, and in particular nitric acid with 59.68% by weight, is used. Preferably, a mixture of nitric acid and phosphoric acid is used. The alumina source, used for the preparation of the suspension, is preferably selected from the group that is formed by hydrargillite, bayerite, pseudo-boehmith, amorphous gels, so-called transition aluminas that comprise at least one phase that is taken in the group that comprises the phases rhô, chi, eta, gamma, kappa, theta and alpha. Very preferably, said alumina source is a pseudo-boehmite, for example the PURAL SB3® that is marketed by the SASOL Company. The preparation of the suspension is continued by introducing at least one zeolite, in powder form, into the mixture that contains water, acid, and the aluminum source, at ambient temperature. The zeolite that is used for the preparation of the suspension can be found in its raw synthesis form just as well as in exchanged form or in calcined form (hydrogen form). The preparation of the suspension ends by the introduction of the emulsion that is prepared during stage a) into the mixture {water, acid, alumina source, zeolite}. Said suspension is stirred vigorously until the viscosity of said suspension is between 250 and 400 mPa·s. The vigorous stirring is preferably carried out between 1,100 and 1,900 rpm and very preferably between 1,400 and 1,700 rpm for about ten minutes, generally between 10 and 15 minutes, and then the stirring speed is reduced preferably to be between 550 and 700 rpm until the viscosity of said suspension is between 250 and 400 mPa·s. Thus, the suspension has suitable rheological properties for being passed through nozzles of the draining pot used during stage c) for shaping the catalyst by drop coagulation. The viscosity of said suspension is measured by means of a plane-plane rheometer for a shear speed gradient of 100 s$^{-1}$. The measured viscosity is the relative viscosity.

The stirring speeds are those obtained by means of a stirring mechanism ER550 of the Euromélanges Company. The engine operates at single-phase direct current of 220 volts; the power is equal to 0.55 kW at 3,000 rpm.

According to the process for preparation of the catalyst that is used in the process for production of light olefins according to the invention, the quantities of different reagents present in the emulsion and in the suspension are such that:

The ratio of pore-forming agent that is equal to the mass of pore-forming agent to the mass of water engaged in the emulsion and the water engaged in the suspension is between 1.5 and 8% by mass, preferably between 2 and 7.5% by mass. The water that is present in the compounds engaged in the emulsion and the suspension, in particular the alumina source and zeolite, does not play a role for the calculation of the level of pore-forming agent.

The proportion of surfactant, present in the emulsion and calculated as being equal to the mass of surfactant, to the mass of pore-forming agent is between 1 and 10% by mass, preferably between 4 and 8% by mass, and very preferably between 5 and 7% by mass, 7 being excluded from the range of 5-7.

The proportion of water that is present in the suspension (after the introduction of the emulsion into the suspension) is such that the ratio of dry mass (corresponding to the mass of powder, namely the source of alumina and the zeolite, dehydrated) to the mass of total water is between 20 and 30% by mass, preferably between 24 and 28% by mass.

The quantity of water, engaged in the emulsion, represents from 9 to 11% by weight of the total quantity of water engaged in the suspension.

The level of acid, engaged in the suspension, equal to the product of the concentration (% by weight) of said acid by the mass of said acid relative to the dry mass of the source of alumina is between 10 and 15% by mass.

The proportion of zeolite, present in the suspension, and calculated as being equal to the ratio of the dry mass of the zeolite to the dry mass of the alumina source and of the zeolite is between 10 and 55% by mass, preferably between 30 and 55% by mass, and very preferably between 35 and 50% by mass.

The proportion of phosphoric acid, advantageously introduced with nitric acid, is such that the ratio by mass of $P_2O_5$/dried alumina source is between 1 and 5% by mass.

The dry mass of the alumina source and that of the zeolite are accessible by measurement of the fire loss (PAF) of each of these powders.

During a first stage i), the shaping by drop coagulation consists in passing said suspension that is prepared during stage b) into a draining pot that consists of nozzles, whereby each of said nozzles has an orifice of a size that is calibrated so as to form droplets. Said draining pot is placed at the top of a column that contains an upper phase that consists of an organic phase and a lower phase that consists of a basic aqueous phase, whereby the organic phase-aqueous phase interface consists of a surfactant. Said nozzles each have an orifice of a size that is calibrated so as to form droplets with a diameter of between about 2 and 3 mm. The dimension of the droplets that are obtained depends not only on the inside diameter of the nozzles (wetting phenomenon), which is generally close to 1 mm, but also on the form with circular section of said nozzles at their ends. The thus formed droplets pass through, according to stage ii) of the shaping by drop coagulation, according to a downward motion, whereby said column contains an upper phase that consists of an organic phase and a lower phase that consists of an aqueous phase, whereby the organic phase-aqueous phase interface consists of a surfactant, so as to collect spherical balls that have a diameter of between about 2 and 3 mm. Said organic phase is selected in such a way that it has a density that is slightly less than that of water. Preferably, the organic phase is selected in such a way that the mass by volume is between 0.7 and 0.9 kg·m$^{-3}$ at 15° C. Said organic phase is selected in such a way that the surface tension between said organic phase and said basic aqueous phase is high, generally between $60.10^{-3}$ and $80.10^{-3}$ N/m. Advantageously, a petroleum fraction, preferably a paraffinic kerosene fraction, in particular Isane®, is selected as an organic phase. The surfactant that separates the organic and aqueous phases is preferably a cationic surfactant. Preferably, the ammonyl BR1244™, an alkyl dimethyl benzyl ammonium bromide in aqueous solution, marketed by the SEPIC SA Company, is used. The basic aqueous phase that constitutes the lower part of the column is advantageously a basic solution that has an ammonia concentration of between 25 and 33 g·l$^{-1}$, preferably between 27 and 29 g·l$^{-1}$. Said basic aqueous solution has a pH of between 8 and 10.

The column, used for shaping by drop coagulation, is prepared by introducing therein first said organic phase, preferably Isane®, and then said basic aqueous solution, preferably said ammoniacal solution, and finally said surfactant, preferably ammonyl BR 1244. Said surfactant can be either directly introduced into said basic aqueous solution or introduced into said column by continuous injection. The volume of said column consists of up to 1% by volume of said surfactant, up to 4% volume of air, from 6 to 10% by volume of said organic phase, with the remainder being occupied by said basic aqueous phase.

The speed at which the droplets fall in the column is such that they preserve their spherical shape so as to obtain spherical balls that have a diameter of between 1 and 3 mm, preferably between 1.8 and 2.2 mm. The droplets, subjected to van der Waals forces by passing through said aqueous solution, are stiffened by aggregating on one another. This gives rise to the formation of balls at the output of said column. Said balls are then driven by a flow of said basic aqueous phase, preferably by a flow of ammonia, recovered and separated from said aqueous phase on a sieve. The ammoniacal aqueous solution that is recovered is advantageously recycled in said column that is used for shaping by drop coagulation.

According to stage d) of the process for preparation of the catalyst that is used in the process for production of light olefins according to the invention, said balls are dried in a ventilated box at ambient temperature and then are dried in a furnace at a temperature of between 60 and 120° C. The drying in the box and the drying in the furnace each generally last between 10 and 20 hours.

The balls are then calcined, according to stage e) of the process for preparation of the catalyst that is used in the process for production of light olefins according to the invention, at a temperature of between 500 and 800° C., preferably between 550 and 700° C. The calcination generally lasts for several hours, preferably between 3 and 5 hours.

The reaction unit that is provided with at least said catalyst in the form of spherical balls used for the implementation of said stage 1) of the process according to the invention operates either in a moving bed or in a fixed bed, preferably in a fixed bed. When it operates in a fixed bed or in a moving bed, the catalyst is periodically regenerated and said unit alternately carries out the reaction for the production of C3-C6 light olefins and the regeneration of said catalyst so as to eliminate the coke that is deposited on its surface during the reaction. The regeneration phase generally comprises a phase for combustion of the carbon deposits formed on the catalyst, for example using an air/nitrogen mixture or oxygen-poor air (in particular by recirculation of smoke) or simply air, whereby said combustion phase generally uses a temperature of between 400° C. and 650° C., whereby the pressure is most often close to the pressure that is used in the reaction unit. Said combustion phase is followed by calcination under dry air, optionally diluted with nitrogen, at a temperature of between 500 and 600° C.

At the end of the implementation of stage 1) of the process according to the invention, a gas effluent that comprises the desired C3-C6 light olefins as well as aromatic compounds, naphthenes, paraffins and olefins that have more than 6 carbon atoms per molecule are obtained.

According to stage 2) of the process for production according to the invention, the gas effluent that is obtained from said reaction unit that is implemented in said stage 1) is fractionated so as to separately collect at least one gaseous fraction that comprises said desired C3-C6 light olefins, at least one organic liquid fraction that comprises organic compounds that have a boiling point that is less than 150° C., and at least one aqueous liquid effluent. Fractionation is done by any method that is known to one skilled in the art. It is conducted by, for example, the successive implementation of pressure relief, distilling columns, or decanters.

The gaseous fraction that comprises said C3-C6 light olefins, obtained at the end of said stage 2) of the process according to the invention, can also contain light paraffins, in particular methane, but also ethane and propane, iso- and n-butane, iso- and n-pentane, and hexane. The majority of said gaseous fraction comprises olefins that advantageously represent at least 70% by weight, preferably at least 85% by weight, of said fraction and can comprise paraffins in a proportion that goes up to 10% by weight of said gaseous fraction. Said gaseous fraction can also contain traces (<1% by weight) of aromatic compounds, in particular benzene, toluene and xylenes. One of the advantages of the process according to the invention resides in the small proportion of ethylene of said gaseous fraction, generally less than 12% by weight, allowing the upgrade of the latter without needing to initiate a subsequent separation stage of ethylene, which is difficult to implement.

The organic liquid fraction, obtained at the end of said stage 2) of the process according to the invention, comprises organic compounds that have a boiling point that is lower than 150° C. Said organic liquid fraction comprises in particular aromatic compounds, in particular benzene, toluene and xylenes, naphthenes (cyclopentane, methylcyclopentane and cyclohexane in particular), paraffins that for the most part have more than 6 carbon atoms per molecule, and olefins that have for the most part more than 6 carbon atoms per molecule.

The distribution of the effluents with an organic nature that are obtained at the end of said stage 2) of the process of the invention is such that the organic gaseous fraction that comprises the desired light olefins represents at least 80% by weight, and the organic liquid fraction, comprising compounds that are produced by undesirable consecutive reactions, represents less than 20% by weight of all of the effluents of an organic nature. The predominant production of C3-C6 light olefins at the expense of other organic compounds shows the optimum selectivity of the process according to the invention. The selectivity of the process according to the invention is also observed by the production of organic effluents (liquid+gas) that are low in aromatic compounds, which are produced by undesirable consecutive reactions.

The following examples illustrate the invention.

EXAMPLE 1 (Invention)

Preparation of the Catalyst C1 that has a Level of Pore-Forming Agent that is Equal to 2.0% by Mass An emulsion is prepared by introducing the following into a one-liter beaker: 244 g of water, 49 g of pore-forming agent that consists of isane, and 2.9 g of surfactant that consists of galoryl. The mixture is put on stir at 500 rpm for 15 minutes.

A suspension is prepared by introducing the following into a 4-liter beaker: 2,198 g of permuted water and 69 g of nitric acid at 59.68% by weight, whereby the mixture is stirred at 400 rpm for 5 minutes. 450 g of PURAL SB3 (fire loss=26.10%) is then added, and the mixture {permuted water, nitric acid, and PURAL SB3} is stirred at 1,600 rpm for 14 minutes. 332 g of ZSM-5 zeolite in H form of the Si/Al ratio that is equal to 140, marketed by the Zeolyst Company, is then added to the mixture {permuted water, nitric acid, and PURAL SB3}, the resulting mixture is stirred at 1,600 rpm for 3 minutes, and then the emulsion, formed by water, isane, and galoryl, is added to said mixture. The combination is stirred at 1,600 rpm for 13 minutes, and then the stirring speed is decreased to 625 rpm for 70 minutes. The viscosity of said mixture is then measured by means of a plane-plane rheometer for a shear speed gradient of 100 s$^{-1}$ and is equal to 270 mPa·s.

For shaping by drop coagulation, a 9.4-liter glass column is used. Said column is charged with 7 liters of an ammonia solution that has a concentration equal to 28 g/l, 0.4 liter of an ammonyl solution that is 1% by mass, and 0.7 liter of isane. The column is topped with a draining pot that consists of nozzles, each one being equipped with a circular orifice that has a diameter that is equal to 1 mm. The suspension is introduced into said draining pot, whereby the draining flow rate is such that 80 droplets are drained per minute and per nozzle. The droplets then fall into the isane phase and then into the ammonia phase at 28 g/l, whereby the isane phase/ammonia phase interface consists of ammonyl. The balls that are thus obtained are placed in a ventilated box at ambient temperature for one night to carry out a first gentle drying and then are placed in a furnace for one night at 100° C. The dried balls are calcined for 2 hours in a muffle furnace at 600° C. The catalyst C1 whose textural and mechanical characteristics are provided in Table 1 is thus obtained. It has a mechanical resistance such that the grain-to-grain crushing (EGG) is equal to 26 N.

EXAMPLE 2 (Invention)

Preparation of the C2 Catalyst that has a Level of Pore-Forming Agent that is Equal to 4.0% by Mass An emulsion is prepared by introducing the following into a one-liter beaker: 247 g of water, 99 g of pore-farming agent consisting of isane, and 5.9 g of surfactant that consists of galoryl. The mixture is put on stir at 500 rpm for 15 minutes.

A suspension is prepared by introducing the following into a 4-liter beaker: 2,219 g of permuted water and 73 g of nitric acid at 59.68% by weight, whereby the mixture is stirred at 400 rpm for 5 minutes. 450 g of PURAL SB3 (fire loss=26.10%) is then added, and the mixture {permuted water, nitric acid, and PURAL SB3} is stirred at 1,600 rpm for 14 minutes. 343 g of the ZSM-5 zeolite in H form that has an Si/Al ratio that is equal to 140 and is marketed by the Zeolyst Company is then added to the mixture {permuted water, nitric acid and PURAL SB3}, the resulting mixture is stirred at 1,600 rpm for 3 minutes, and then the emulsion that is formed from water, isane, and galoryl is added to said mixture. The combination is stirred at 1,600 rpm for 13 minutes, and then stirring speed is reduced to 625 rpm for 70 minutes. The viscosity of said mixture is then measured by means of a plane-plane rheometer for a shear speed gradient of 100 s$^{-1}$ and is equal to 320 mPa·s.

For shaping by drop coagulation, a 9.4-liter glass column is used. Said column is charged with 7 liters of an ammonia solution that has a concentration equal to 2.8 g/l, 0.4 liter of an ammonyl solution with 1% by mass, and 0.7 liter of isane. The column is topped with a draining pot that consists of nozzles, each one being equipped with a circular orifice that has a diameter that is equal to 1 mm. The suspension is introduced into said draining pot, whereby the draining pot is such that 80 droplets are drained per minute and via nozzle. The droplets then fall into the isane phase, and then into the ammonia phase at 28 g/l, whereby the isane phase-ammonia phase interface consists of ammonyl. The thus obtained balls are placed in a box that is ventilated at ambient temperature for one night to carry out a first gentle drying and then are placed in a furnace for one night at 100° C. The dried balls are calcined for 2 hours in a muffle furnace at 600° C. The C2 catalyst whose textural and mechanical characteristics are provided in Table 1 is thus obtained. It has a mechanical resistance such that the grain-to-grain crushing (EGG) is equal to 16 N.

EXAMPLE 3 (Invention)

Preparation of the C3 Catalyst that has a Level of Pore-Forming Agent that is Equal to 7.5% by Mass An emulsion is prepared by introducing the following into a one-liter beaker: 249 g of water, 187 g of pore-forming agent that consists of isane, and 11.2 g of surfactant that consists of galoryl. The mixture is placed on stir at 500 rpm for 15 minutes.

A suspension is prepared by introducing the following into a 4-liter beaker: 2,243 g of permuted water and 68 g of nitric acid with 59.68% by weight, whereby the mixture is stirred at 400 rpm for 5 minutes.

450 g of PURAL SB3 (fire loss=26.10%) is then added, and the mixture {permuted water, nitric acid, and PURAL SB3} is stirred at 1,600 rpm for 14 minutes. 339 g of ZSM-5 zeolite in H form with an Si/Al ratio that is equal to 140 and marketed by the Zeolyst Company is then added to the mixture {permuted water, nitric acid, and PURAL SB3}, the resulting mixture is stirred at 1,600 rpm for 3 minutes, and then the emulsion that is formed by water, isane and galoryl is added to said mixture. The combination is stirred at 1,600 rpm for 13 minutes, and then the stirring speed is decreased to 625 rpm for 70 minutes. The viscosity of said mixture is then measured by means of a plane-plane rheometer for a shear speed gradient of 100 s$^{-1}$ and is equal to 270 mPa·s.

For the drop coagulation shaping, a 9.4-liter glass column is used. Said column is charged with 7 liters of an ammonia solution that has a concentration equal to 28 g/l, 0.4 liter of an ammonyl solution with 1% by mass, and 0.7 liter of isane. The column is topped with a draining pot that consists of nozzles, each one being equipped with a circular orifice that has a diameter that is equal to 1 min. The suspension is introduced into said draining pot, whereby the draining flow rate is such that 80 droplets are drained per minute and via nozzle. The droplets then fall into the isane phase, and then into the ammonia phase at 28 g/l, whereby the isane phase-ammonia phase interface consists of ammonyl. The thus-obtained balls are placed in a ventilated box at ambient temperature for one night to carry out a first gentle drying and then are placed in a furnace for one night at 100° C. The dried balls are calcined for 2 hours in a muffle furnace at 600° C. The C3 catalyst whose textural and mechanical characteristics are provided in Table 1 is thus obtained. It has a mechanical resistance such that the grain-to-grain crushing (EGG) is equal to 26 N.

EXAMPLE 4 (For Comparison)

Preparation of the C0 Catalyst in the Absence of Pore-Forming Agent

A suspension is prepared by introducing the following into a 4-liter beaker: 2,492 g of permuted water and 68 g of nitric acid at 59.76% by weight, whereby the mixture is stirred at 400 rpm for 5 minutes. 450 g of PURAL SB3 (fire loss=26.10%) is then added, and the mixture {permuted water, nitric acid, and PURAL SB3} is stirred at 1,600 rpm for 14 minutes. 339 g of ZSM-5 zeolite in H form of the Si/Al ratio that is equal to 140 and marketed by the Zeolyst Company is then added to the mixture {permuted water, nitric acid, and PURAL SB3}, the resulting mixture is stirred at 1,600 rpm for 16 minutes, and the stirring speed is decreased to 625 rpm for 70 minutes. The viscosity of said mixture is then measured by means of a plane-plane rheometer for a shear speed gradient of $100\ s^{-1}$ and is equal to 270 mPa·s.

For shaping by drop coagulation, a 9.4-liter glass column is used. Said column is charged with 7 liters of an ammonia solution that has a concentration equal to 28 g/l, 0.4 liter of an ammonyl solution with 1% by mass, and 0.7 liter of isane. The column is topped with a draining pot that consists of nozzles, whereby each one is equipped with a circular orifice that has a diameter that is equal to 1 mm. The suspension is introduced into said draining pot, whereby the draining flow rate is such that 80 droplets are drained per minute and via nozzle. The droplets then fall into the isane phase, and then into the ammonia phase at 28 g/l, whereby the isane phase-ammonia phase interface consists of ammonyl. The thus obtained balls are placed in a ventilated box at ambient temperature for one night to carry out a first gentle drying and then are placed in a furnace for one night at 100° C. The dried balls are calcined for 2 hours in a muffle furnace at 600° C. The C0 catalyst, not in accordance with the invention, whose textural and mechanical characteristics are provided in Table 1, is thus obtained.

The textural and mechanical characteristics of the C0, C1, C2 and C3 catalysts are provided in Table 1 below.

TABLE 1

Textural and Mechanical Characteristics of the C0, C1, C2 and C3 Catalysts

|  | C0 | C1 | C2 | C3 |
|---|---|---|---|---|
| BET Surface Area (m²/g) | 326 | 321 | 329 | 323 |
| Hg Pore Volume (ml/g) | 0.30 | 0.41 | 0.47 | 0.49 |
| HG Macropore Volume (ml/g) | 0.005 | 0.12 | 0.18 | 0.14 |
| Hg Mesopore Volume (ml/g) | 0.29 | 0.29 | 0.29 | 0.35 |
| Size of Spherical Balls (mm) | 1.8-2.2 | 1.8-2.2 | 1.8-2.2 | 1.8-2.2 |

EXAMPLE 5

Catalytic Performances of the C0, C1, C2 and C3 Catalysts in a Process for the Production of Light Olefins from Ethanol Four separate tests are initiated to evaluate the catalytic performances of each of the C0 to C3 catalysts.

For each test, a reaction unit that operates in a flow-through fixed bed is charged with 15 cm³ of C1, C2, C3 or C0 catalyst (iso-height of the reactive bed).

Before the start-up of each catalytic test, the activation of each of the catalysts involved is initiated at 550° C. under air for 2 hours. This activation consists of a drying of the catalyst before its use, and a calcination whose purpose is the combustion of traces of oil and grease that may be present.

The feedstock that supplies said reaction unit, for each of the 4 catalytic tests, is a feedstock that contains 50% by weight of dilute absolute ethanol (99.9%) in 50% by weight of bi-permuted water.

For each test, 20 g/h of feedstock is injected in the catalyst. The reaction conditions that are used are the following: a temperature of 515° C., whereby the reactor is isothermic, and a pressure of 0.15 MPa. At the output of the reaction unit, the separation of the gas phase, the organic liquid phase, and the aqueous liquid phase is initiated by a double separation phase, whereby the first separator evacuates the gas that is formed, and the second separator is a Florentine-type system that separates the light liquid phase from the heavy liquid phase by differences in density. Each of said phases (gas and liquid) is analyzed through a gas-phase chromatograph.

The catalytic performances that are obtained by each of the C0, C1, C2 and C3 catalysts during tests described above are provided in Table 2.

The composition of the effluents appearing in Table 2 corresponds to the mean composition of the effluents after 2 hours of reaction.

TABLE 2

Catalytic Performances Achieved by Each of the C0, C1, C2 and C3 Catalysts

| Catalyst<br>Operating Conditions | C0 | C1 | C2 | C3 |
|---|---|---|---|---|
| T (° C.) | 515 | 515 | 515 | 515 |
| P (MPa) | 0.15 | 0.15 | 0.15 | 0.15 |
| pph (h⁻¹) EtOH | 2 | 2 | 2 | 2 |
| Reaction Time (h) | 2 | 2 | 2 | 2 |
| Ethanol Conversion (%) | 99.4 | 99.8 | 99.8 | 99.4 |
| Distribution of Organic Products (Outside of the Aqueous Phase) | % by Weight | % by Weight | % by Weight | % by Weight |
| Gas | 76.7 | 84.2 | 85.2 | 94.5 |
| Liquid (Eb < 150° C.) | 23.3 | 15.8 | 14.8 | 5.5 |

TABLE 2-continued

Catalytic Performances Achieved by Each of the C0, C1, C2 and C3 Catalysts

| Gas-Phase Composition (Hydrocarbons outside of CO, CO$_2$, H$_2$O, H$_2$) | % by Volume | % by Volume | % by Volume | % by Volume |
|---|---|---|---|---|
| C1 (CH$_4$) | 1.2 | 1.3 | 1.3 | 1.2 |
| C2 (Primarily Ethylene) | 16.6 | 8.7 | 10.4 | 11.9 |
| C3 | 18.0 | 28.0 | 27.3 | 27.7 |
| C4 | 42.0 | 38.0 | 40.0 | 37.0 |
| C5 | 9.7 | 16.0 | 14.0 | 15.0 |
| C6 | 12.5 | 8.0 | 7.0 | 7.2 |
| % by Mass of Aromatic Compounds Present in the Organic Effluents (Gas + Liquid) (Outside of the Aqueous Phase) | 10.5 | 6.5 | 5.2 | 4.5 |
| C3-C6 Olefin Yield (%) | 69.7 | 80.0 | 80.2 | 88.1 |

The C2 compound that is obtained in the gaseous fraction is primarily ethylene. The C3 to C6 compounds that are obtained in the gaseous fraction are primarily C3-C6 light olefins, corresponding to the products that are desired for the implementation of the process of the invention.

The organic compounds that are present in the liquid fraction and that have a boiling point (Eb) that is less than 150° C. are essentially aromatic compounds (benzene, toluene, xylenes), naphthenes, and C6, C7 and C8 olefins. Said compounds are produced by consecutive and non-selective reactions and are consequently undesirable.

The results that appear in Table 2 show that the C1, C2 and C3 catalysts are more active for the conversion of ethylene into C3-C6 light olefins than the C0 catalyst that is prepared in the absence of the pore-forming agent. The effect is an increased proportion of the C3-C6 olefins in the gaseous fraction, thereby resulting in a significantly improved yield in terms of the desired olefins. Furthermore, the distribution of organic effluents (liquid+gas) demonstrates that the implementation of the process for the production of C3-C6 light olefins in the presence of C1, C2 and C3 catalysts leads to the mass production of a gas phase that is greater than that obtained in the presence of the C0 catalyst, which promotes the production of compounds that are present in the organic liquid fraction and obtained from non-selective reactions, to the detriment of the C3-C6 light olefins. The C1, C2 and C3 catalysts are therefore more selective than the C0 catalyst. The best selectivity of the C1, C2 and C3 catalysts leads, on the other hand, to a reduced production of aromatic compounds, produced at the end of undesirable reactions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application Ser. No. 09/03.910, filed Aug. 7, 2009, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of C3-C6 light olefins from ethanol comprising at least:
 1) Passing a gaseous feedstock that contains at least 10% by mass of ethanol into at least one reaction unit provided with at least one catalyst in the form of spherical balls with a diameter of between 1 and 3 mm, whereby each of said spherical balls comprises at least one zeolite and at least one alumina-based substrate such that the proportion of zeolite is 15 to 90% by weight and the remainder consists essentially of alumina, and has a pore distribution such that the macropore volume measured by mercury porosimetry is between 0.10 and 0.20 ml/g, and the mesopore volume measured by mercury porosimetry is between 0.25 and 0.35 ml/g, so as to produce at least one gas effluent that comprises at least said C3-C6 light olefins, and
 2) Fractionating of the gas effluent obtained in a stage 1) so as to collect at least one gaseous fraction comprising said light olefins, at least one organic liquid fraction comprising compounds having a boiling point less than 150° C. and at least one aqueous liquid effluent.

2. A process for production according to claim 1, wherein each of said spherical balls has macroporous fields above 50 nm.

3. A process for production according to claim 1, wherein said catalyst is in the form of spherical balls with a diameter of between 1.8 and 2.2 mm.

4. A process for production according to claim 1, wherein said zeolite present in each of said spherical balls is selected from among the zeolites of the structural type MEL, MFI, NES, EUO, FER, CHA, MFS, MWW and NES.

5. A process for production according to claim 4, wherein said zeolite is an MFI- structural-type zeolite.

6. A process for production according to claim 1, wherein said catalyst is prepared according to a process that comprises a) the preparation of at least one emulsion that is formed by at least one pore-forming agent, water, and a surfactant, b) the preparation of a suspension that is formed by water, acid, an alumina source, at least one zeolite, and said emulsion that is prepared during stage a), c) the shaping by drop coagulation comprising in i) passing said suspension that is formed in b) into a draining pot that comprises nozzles that each have an orifice of calibrated size so as to form droplets, ii) passing, in a downward motion, said droplets into a column that contains an upper phase that comprises of an organic phase and a lower phase that comprises a basic aqueous phase, and an organic phase-aqueous phase interface comprising a surfactant, so as to collect spherical balls, d) the drying of said balls, and e) the calcination of said balls.

7. A process for production according to claim 6, wherein said pore-forming agent, used for the preparation of the emulsion according to said stage a), is a paraffinic kerosene fraction that has 10 to 14 carbon atoms, formed by normal paraffin and iso-paraffins, and having a boiling point of between 220 and 350° C.

8. A process for production according to claim 6, wherein emulsion has a ratio of the pore-forming agent that is equal to the mass of the pore-forming agent to the mass of the water that is engaged in the emulsion and the water that is engaged in the suspension is between 1.5 and 8% by mass.

9. A process for production according to claim 6, wherein the acid, engaged in the suspension, in step (b) is based on the total of the mass of said acid added to the dry mass of the alumina source, is between 10 and 15% by mass.

10. A process for production according to claim 1, wherein said feedstock comprises ethanol and water, whereby ethanol represents at least 10% by mass of the dilute feedstock.

11. A process for production according to claim 10, wherein said feedstock comprises at least 50% by weight of water.

12. A process for production according to claim 1, wherein said feedstock consists entirely of ethanol.

13. A process for production according to claim 1, wherein said reaction unit operates at a temperature of between 300 and 600° C., under a pressure of between 0.1 and 1.5 MPa, with an hourly rate of (feedstock weight per weight of catalyst per hour) of between 0.1 and 10 $h^{-1}$.

14. A process for production according to claim 1, wherein said gaseous fraction that is obtained from said stage 2) has a proportion of ethylene of less than 12% by weight.

15. A process according to claim 1, wherein the proportion of zeolite in the spherical balls is 30-80% by weight.

16. A process according to claim 1, wherein the proportion of zeolite in the spherical balls is 35-50% by weight and the ethanol represents at least 40% of the feedstock by mass.

* * * * *